United States Patent [19]

Hovis

[11] Patent Number: 4,962,268
[45] Date of Patent: Oct. 9, 1990

[54] ALKYLATION CATALYST ISOLATION

[75] Inventor: Keith W. Hovis, Bartlesville, Okla.

[73] Assignee: Phillips Petroleum Company, Bartlesville, Okla.

[21] Appl. No.: 314,676

[22] Filed: Feb. 22, 1989

[51] Int. Cl.⁵ .............................................. C07C 2/56
[52] U.S. Cl. ............................. 585/705; 585/709; 585/716; 585/719; 422/140
[58] Field of Search ............... 208/80; 585/705, 706, 585/709, 719, 720, 723, 716

[56] References Cited

U.S. PATENT DOCUMENTS

| | | | |
|---|---|---|---|
| 3,005,034 | 10/1961 | Edison et al. | 585/716 X |
| 3,158,661 | 11/1964 | Plaster et al. | 585/719 X |
| 3,213,157 | 10/1965 | Hays et al. | 585/719 X |
| 3,544,651 | 5/1968 | Chapman | 260/683.45 |
| 3,763,266 | 8/1971 | Henderson | 260/683.43 |
| 4,218,575 | 8/1980 | Webb, Jr. | 585/719 X |
| 4,423,277 | 12/1983 | Stroud | 585/719 |
| 4,579,998 | 4/1986 | Hutson, Jr. | 585/716 |

Primary Examiner—Glenn Caldarola
Attorney, Agent, or Firm—Charles W. Stewart

[57] ABSTRACT

In an alkylation process wherein the amount of hydrogen fluoride (HF) acid catalyst required to maintain a desired HF acid/hydrocarbon ratio in a plurality of alkylation reactors is contained in the lower portion of a common settler vessel, the improvement comprises: dividing the lower portion of the common settler vessel into a plurality of chambers for containing the desired amount of HF acid catalyst, such that a leak affecting the catalyst handling system for one of the plurality of reactors would only spill the amount of liquid HF acid contained in one of the chambers, and would not affect the liquid HF acid level in a non-leaking chamber.

12 Claims, 4 Drawing Sheets

1

ALKYLATION CATALYST ISOLATION

This invention relates generally to method and apparatus for handling fluids. In one aspect it relates to apparatus for fluid handling in an alkylation process. In another aspect it relates to a method for reducing spillage of acidic material in the event of a leak in an alkylation process.

BACKGROUND OF THE INVENTION

It is common practice in the petroleum industry to produce high octane motor fuel by alkylating an isoparaffine with an olefin in the presence of a catalyst which preferably is liquid hydrofluoric acid or hydrogen fluoride (HF). Such a process is commonly knonw as an HF alkylation process or merely an alkylation process. The effluent from the alkylation reactor containing hydrocarbon and acid, is usually passed to a generally vertical arranged settler vessel at an intermediate point along the length of the settler vessel. A hydrocarbon phase is separated from an acid phase in the settler vessel, with the hydrocarbon phase contained in the upper portion of the settler vessel and the acid phase contained in a lower portion of the settler vessel. Accordingly, a liquid-liquid interface between the acid phase and hydrocarbon phase is formed within the settler vessel. As used herein, the liquid-liquid interface is located at a point along the height of the settler vessel where the acid concentration of the material in the settler vessel is greater by a predetermined amount than the acid concentration in the alkylate product supplied to the settler from the reactor. The hydrocarbon phase is fractioned to separate low boiling hydrocarbons from the alkylate product while the acid phase is cooled and recycled to the alkylation reactor for reuse in the alkylation process. As necessary, acid catalyst can be withdrawn from the system for purification. The purified acid catalyst and, as necessary, additional fresh acid is returned to the alkylation reactor.

It is known to improve the economics of an alkylation process by employing two or more alkylation reactors and passing the individual alkylate product streams to a common settler vessel, thereby forming a common pool of acid catalyst in the lower portion of the common settler vessel. Acid catalyst is then withdrawn from the common pool and passed in individual streams to the respective alkylation reactors. While an alkylation system employing multiple reactors and a common acid catalyst pool is effective for reducing equipment cost while maintaining a desired hydrocarbon/catalyst ratio for each reactor, and is also effective for increasing production of high quality gasoline boiling range materials, the system presents certain safety considerations. For example, with a common acid catalyst pool, a leak in one reactor could result in spillage of the entire catalyst pool which supplies the multiple reactors.

Acid catalyst fluid handling systems associated with alkylation processes are designed with due concern for providing a non-leaking catalyst fluid handling system. In order to provide greater safety, however, it is desirable to reduce, as much as possible, the spillage that would occur in the event of a leak affecting the liquid acid catalyst.

Accordingly, it is an object of this invention to improve safety in operating an alkylation process.

A further object of this invention is to increase the safety of a petroleum refining process and the apparatus employed therein.

Another object of this invention is to provide apparatus and method for reducing the spillage of acid catalyst in the invent of a leak in the acid catalyst handling system associated with an alkylation process.

SUMMARY OF THE INVENTION

In accordance with one aspect of this invention, multiple chambers are provided in the bottom of a common acid settler vessel to contain the acid catalyst. The number of chambers provided at least corresponds to the number of respective reactors which supply alkylate product to the common settler vessel. Separate acid return streams for each reactor are also provided so that a leak in one reactor, or its associated acid cooler, would result in liquid spillage of no more than the amount of the acid catalyst in the chamber of the common settler vessel associated with that reactor.

In accordance with another aspect of this invention the common settler vessel is operated with both liquid and gaseous hydrocarbon phases at lower pressures, so that the leak rate resulting from a leak in a reactor would be minimized.

In a preferred embodiment of this invention a common settler vessel is provided with at least one baffle extending from wall to wall at the bottom of the common settler vessel and upwardly into close proximity, or above, the interface between the liquid acid catalyst phase and the liquid hydrocarbon phase in the common settler vessel. The baffle separates the lower portion of the settler vessel into two or more chambers and prevents liquid communication between the quantities of liquid acid catalyst which are contained within the chambers and are to be recycled to the respective reactors. A separate outlet is provided for each chamber in the bottom of the common settler vessel for return of the acid catalyst to the respective reactor and associated cooler.

Should the acid catalyst level lower in one chamber due to leakage or spillage, liquid hydrocarbon from the correspondingly lowered hydrocarbon phase thereabove displaces the acid catalyst volume lost and thus provides a liquid seal for the acid catalyst in the non-leaking chambers. Also, another material which is less dense and of higher boiling point than the acid catalyst, could be injected to replace the spilled acid catalyst and provide the liquid seal.

In a preferred embodiment of the present invention, four reactors, each having an associated cooler, are utilized. Two riser reactors are positioned on two opposite sides of a vertically oriented settler vessel. Alkylate product streams of the two reactors on one side of the settler are combined at or above the elevation of the settler inlet, and enter the settler in a combined stream. In a similar manner the alkylate product of the two reactors on the other side of the settler vessel are combined and enter the settler vessel in a single stream. Four separate streams are provided for returning the acid catalyst from the settler to four corresponding riser reactors via four corresponding acid catalyst coolers.

BRIEF DESCRIPTION OF THE DRAWINGS

Additional objects and advantages of the invention will be apparent from the following detailed description of the preferred embodiment of the invention as illustrated by the drawings in which.

DETAILED DESCRIPTION OF THE PREFERRED EMBODIMENT

Figure 1:
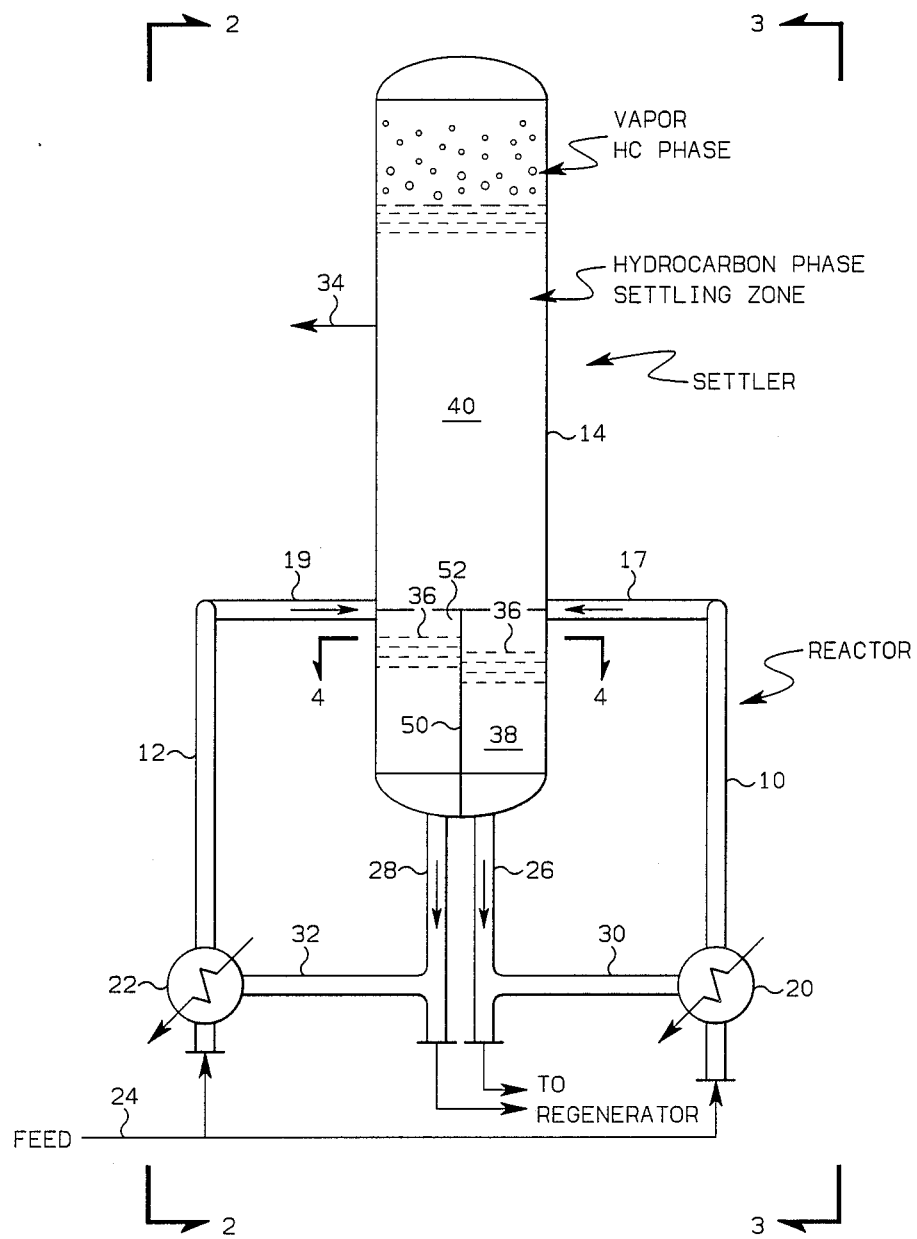
FIG. 1 is a diagrammatic elevation of riser reactors, a setler vessel and coolers provided in an arrangement suitable for carrying out the invention.
Figure 2:
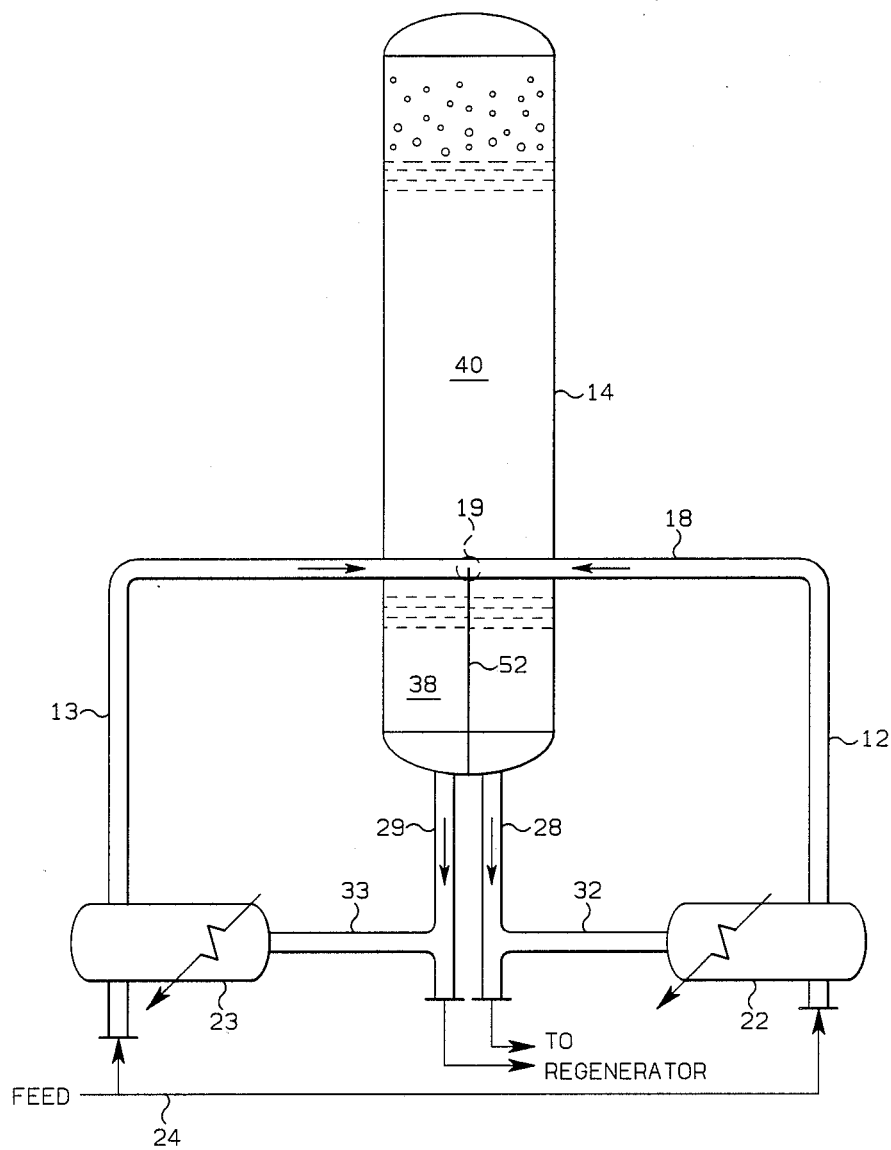
FIG. 2 is a side elevation taken along line 2—2 of FIG. 1.
Figure 3:
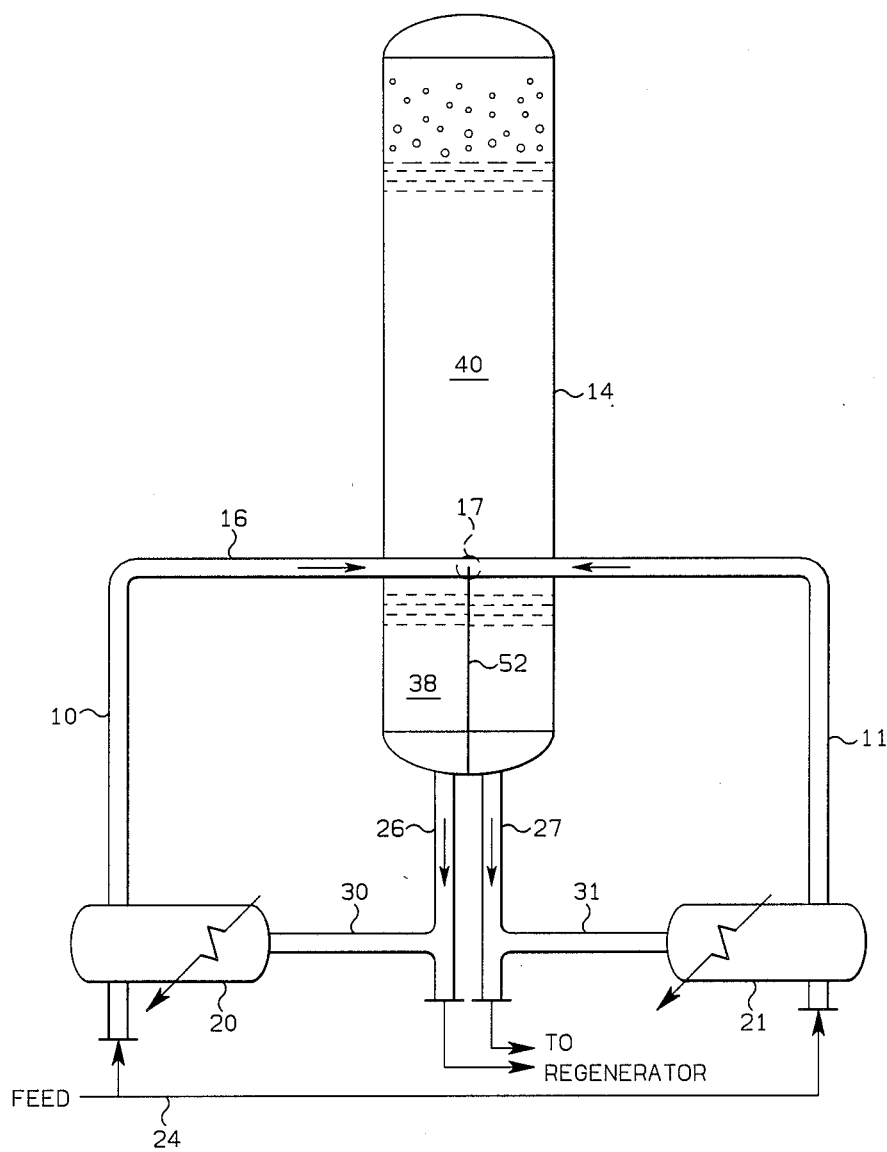
FIG. 3 is a side elevation taken along lines 3—3 of FIG. 1.

In the following discussion, parts which appear in more than one of the drawing figures shall be referred to by the same reference numeral in each of the drawing figures in which the part appears. Referring now to the drawings and in particular to FIGS. 1, 2 and 3, four upwardly extending tubular reactors, referred to hereinafter as riser reactors, are designated by the reference characters 10, 11, 12 and 13 and are in open communication at the tops thereof with a generally vertically disposed settler vessel 14 via conduits 16, 17, 18 and 19. The settler vessel 14 defines a vertically extending separation zone therewithin having a lower portion, an upper portion and an intermediate portion. The settler vessel 14 provides means for separating a mixture containing a heavier liquid and a lighter liquid. Effluent alkylate, together with acid catalyst, is introduced into a lower portion of the settler 14 from the outlets of reactors 110, 11, 12 and 13 through conduits 16, 17, 18 and 19. Although four reactors are illustrated in FIGS. 1–4, any number of reactors can be used in the practice of the invention.

The lower ends of riser reactors 10, 11, 12 and 13 are in open fluid communication with coolers 20, 21, 22 and 23, respectively. Hydrocarbon feed is provided via conduit 24 to coolers 20, 21, 22 and 23 along with additional fresh acid where cooled recycled or rerun acid catalyst is picked up to form a hydrocarbon and acid catalyst mixture. The hydrocarbon and acid catalyst mixture is dispersed upwardly with high velocity through the coolers 20, 21, 22 and 23 and into the corresponding inlets of riser reactors 10, 11, 12 and 13, respectively.

At the bottom of common settler vessel 14, outlet conduits 26, 27, 28 and 29, which extend downwardly from settler vessel 14, are provided for the withdrawal of liquid acid catalyst for recycle. Conduits 26, 27, 28 and 29 are connected at the lower ends thereof with coolers 20, 21, 22 and 23, respectively via corresponding conduits 30, 31, 32 and 33. At an intermediate point along the length of the settler vessel 14 an outlet conduit 34 is provided for the removal of the separated liquid hydrocarbon product.

In operation, a liquid hydrocarbon feed mixture comprising a mixture of an alkylating agent, such as a low boiling olefin, e.g. butylene, and an alkylatable hydrocarbon, such as a low boiling isoparaffin, e.g. isobutane, is introduced through conduit 24, as well as fresh makeup acid catalyst. The feed mixture is dispersed at high velocity in the shells of coolers 20, 21, 22 and 23 which contain cooled liquid acid catalyst, thus inducing acid catalyst circulation into the hydrocarbon feed mixture by density difference between the settled acid 38 from the settler 14 and the fresh makeup acid catalyst dispersed with the hydrocarbon feed. In this manner acid catalyst is picked up by the flow action of the liquid hydrocarbon feed mixture. Hydrocarbon feed mixture and cooled recycled acid catalyst pass through the reactors 10, 11, 12 and 13 in co-current flow which results in formation of higher molecular weight hydrocarbon material or alkylate of increased octane value, as is well known in the art.

Reaction effluent, containing alkylate (i.e. hydrocarbon product), catalyst and unreacted feed hydrocarbon, passes from reactors 10, 11, 12 and 13 and enters settler vessel 14 through conduit 16, 17, 18 and 19. Within settler vessel 14, the effluent from reactors 10, 11, 12 and 13 separates into a lower liquid acid phase and an upper liquid hydrocarbon phase. In accordance with the invention, however, settler vessel 14 is preferably operated with both liquid and gaseous hydrocarbon phases, as illustrated in FIG. 1.

A liquid-liquid interface is formed at a point 36 in settler vessel 14. The interface occurs at the level between the lower heavy acid phase 38 and the lighter hydrocarbon phase 40. As used herein the interface 36 is considered to be the point along the vertical length of the chamber of the common settler vessel 14 where the acid concentration of the material settled in the lower portion of settler vesel 14 is equal to, or greater by a predetermined amount, than the acid concentration in the reactor effluent material supplied to the common settler vessel 14, through conduits 17 and 19.

Figure 4:
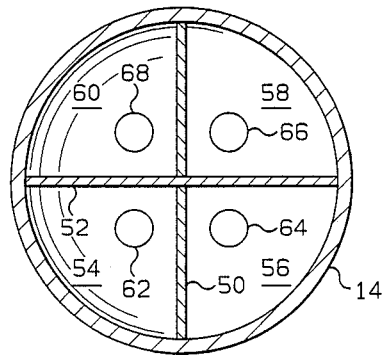
FIg. 4 is a cross sectional view taken along line 4—4 of FIG. 1.

As most clearly illustrated in FIG. 4, the lower portion of common settler vessel 14 is provided with baffles 50 and 52 which divide the lower portion of vessel 14 into four chambers 54, 56, 58, and 60. As illustrated most clearly in FIGS. 1, 2 and 3, the baffles 50 and 52 extend from the bottom of the settler vessel 14, at least into close proximity to the interface level 36. Thus, acid catalyst supplied to settler vessel 14 from a pair of riser reactors on one side of the settler vessel 14, and which descends mostly along the walls of settler vessel 14, is for the most part returned to the respective pair of riser reactors.

An alkylation unit such as shown in the drawings may be operated such that the interface level 36 is different in the various chambers 54, 56, 58 and 60. The baffles 50 and 52 therefore may extend upwardly to near proximity of the interface level in one chamber while extending significantly above the interface level in an adjacent chamber. Accordingly, the baffles 50 and 52 may be any desired height and may extend significantly into the hydrocarbon settling zone 40 if desired. The requirement for the baffles 50 and 52 is that they extend to a height sufficient to assure that the chambers 54, 56, 58 and 60 contain substantially all of the acid catalyst in the lower portion of settler vessel 14.

The acid catalyst is withdrawn from the chambers 54, 56, 58 and 60 through outlets 62, 64, 66 and 68, respectively, illustrated in FIG. 4, which outlets are provided in the bottom of common settler vessel 14 and are connected in fluid flow communication with conduits 28, 26, 27 and 29, respectively, and the acid catalyst is recycled to the riser reactors via the coolers and interconnecting conduits.

The invention is not dependent upon specific reaction conditions, or reactants, as these are conventional and well known in the art. It is, however, as previously stated, desired to operate the common settler 14 less than liquid full and at a low pressure, so as to minimize the leakage rate in the event of a failure.

For reasons of brevity, conventional auxiliary equipment such as pumps, additional feed lines, additional heat exchangers, measurement and control devices, etc.

have not been included in the above description as they play no part in the explanation of the invention.

The invention is thus broadly applicable to containing heavy liquid in a settler vessel. Various modifications of this invention, such as providing additional chambers for the containment of the acid catalyst, can be made in view of the foregoing disclosure and the appended claims. Such variations and modifications are within the scope of the present invention as claimed.

That which is claimed is:

1. Apparatus comprising:
   a vessel defining a separation zone having a lower portion, an intermediate portion and an upper portion for separating a mixture containing a heavier liquid and a lighter liquid;
   means for introducing said mixture containing a heavier liquid and a lighter liquid into said separation zone, to form a liquid-liquid interface in said separation zone, said interface occurring at a level between said heavier liquid and said lighter liquid, and wherein said heavier liquid is contained in said loewr portion of said separatin zone and wherein said means for introducing a mixture comprises reactor means for alkylating olefins with isoparaffins in the presence of a hydrogen fluoride catalyst;
   means for passing reactor effluent comprising liquid hydrogen fluoride catalyst and liquid hydrocarbon product from said reactor means into said separation zone; and
   means disposed within said vessel for dividing said lower portion of said separation zone into a plurality of chambers, for containing at least a major portion of said heavier liquid so that any leak resulting in the drawing of said heavy liquid from any individual chamber of said plurality of chambers will not correspondingly result in the draining of said heavier liquid from the remaining unaffected chambers of said plurality of chambers.

2. Apparatus in accordance with claim 1 wherein said means for dividing comprises:
   a baffle extending upwardly from the bottom of said lower portion of said separation zone to a location proximate said interface.

3. Apparatus in accordance with claim 1 wherein said means for dividing comprises:
   a baffle extending upwardly from the bottom of said lower portion of said separation zone into said intermediate portion of said separation zone.

4. Apparatus comprising:
   a vessel defining a separation zone having a lower portion, an intermediate portion and an upper portion for separating a mixture containing a heavier liquid and a lighter liquid;
   means for introducing said mixture containing a heavier liquid and a lighter liquid into said separation zone, to form a liquid-liquid interface in said separation zone, said interface occurring at a level between said heavier liquid and said lighter liquid, and wherein said heavier liquid is contained in said lower portion of said separation zone and wherein said means for introducing a mixture comprises a plurality of reactor means for reacting olefins with isoparaffins in the presence of a hydrogen fluoride catalyst;
   means for passing reaction effluent comprising liquid hydrogen fluoride catalyst and liquid hydrocarbon product from said plurality of reactor means into said separation zone; and
   means disposed within said vessel for dividing said lower portion of said separation zone into a plurality of chambers, for containing at least a major portion of said heavier liquid so that any leak resulting in the draining of said heavy liquid from any individual chamber of said plurality of chambers will not correspondingly result in the draining of said heavier liquid from the remaining unaffected chambers of said plurality of chambers.

5. Apparatus in accordance with claim 4, additionally comprising:
   means associated with each of said plurality of chambers for withdrawing liquid hydrogen fluoride catalyst from each of said plurality of chambers; and
   means for recycling the liquid hydrogen fluoride catalyst withdrawn from each of said plurality of chambers to a corresponding one of said reactor means.

6. A method for reducing spillage of liquid from a lower portion of a separation zone having an upper portion, a lower portion and an intermediate portion in the event of the occurrence of a leeak which would spill liquid from said lower portion of said separation zone, said method comprising the steps of:
   allowing a mixture containing a heavier liquid and a lighter liquid in said separation zone to separate, wherein a liquid-liquid interface is formed in said separation zone between said heavier liquid and said lighter liquid, and
   dividing said lower portion of said separation zone into a plurality of chambers containing at least a major portion of said heavier liquid so that any leak resulting in the draining of said heavy liquid from any individual chamber of said plurality of chambers will not correspondingly result in the draining of said heavy liquid from the remaining unaffected chambers of said plurality of chambers.

7. A method in accordance with claim 6 wherein said step of dividing said lower portion comprises:
   installing a baffle, wherein said baffle extends upwardly from the bottom of said lower portion of said separation zone to a location proximate said liquid-liquid interface.

8. A method in accordance with claim 6 wherein said step of dividing said lower portion comprises:
   installing a baffle, wherein said baffle extends upwardly from the bottom of said lower portion of said separation zone into said intermediate portion of said separation zone.

9. A method in accordance with claim 6 wherein said heavier liquid comprises a liquid hydrogen fluoride catalyst and said lighter liquid comprises a liquid hydrocarbon product.

10. A method for increasing safety in operating an alkylation process for alkylating olefins with isoparaffins in the presence of a hydrogen fluoride catalyst, wherein said alkylation process employs a plurality of reactors with associated coolers, and a common settler vessel defining a separation zone having a lower portion, an intermediate portion, and an upper portion, and wherein a mixture of liquid acid catalyst and liquid hydrocarbon product is formed in said plurality of reactors and is separated in said common settler vessel, said method comprising the following steps:
    dividing said lower portion of said separation zone into a plurality of chambers so that any leak resulting in the draining of said heavy liquid from any individual chamber of said plurality of chambers will not correspondingly result in the draining of said heavy liquid from the remaining unaffected chambers of said plurality of chambers;

introducing a mixture of a liquid acid catalyst and a liquid hydrocarbon product formed in said plurality of reactors into said separation zone; and allowing said liquid acid catalyst and said liquid hydrocarbon product to separate in said separation zone whereby a liquid-liquid interface is formed in said separation zone at the level between said liquid acid catalyst and said liquid hydrocarbon product, and wherein a major portion of said liquid acid catalyst is contained in said plurality of chambers in said lower portion of said separation zone.

11. In an alkylation process wherein the amount of liquid acid catalyst required to maintain a desired liquid acid catalyst/liquid hydrocarbon product ratio in a plurality of alkylation reactors is contained in the lower portion of a common settler vessel operatively connected to said plurality of alkylation reactors, the improvement comprising:

dividing the lower portion of said common settler vessel into a plurality of chambers for containing a desired amount of liquid acid catalyst so that a leak resulting in the draining of liquid acid catalyst from one of the plurality of alklyation reactors will spill no more than the amount of liquid acid catalyst contained in one of said plurality of chamers and will not affect the liquid acid catalyst level in any of the other of said plurality of chambers.

12. A method in accordance with claim 10 comprising the additional step of:

operating said common setller vessel less than liquid full so as to form a gaseous hydrocarbon phase in said upper portion of said separation zone.

* * * * *

UNITED STATES PATENT AND TRADEMARK OFFICE
CERTIFICATE OF CORRECTION

PATENT NO. : 4,962,268

DATED : Oct. 9, 1990

INVENTOR(S) : Keith W. Hovis

It is certified that error appears in the above-identified patent and that said Letters Patent is hereby corrected as shown below:

In claim 1, column 5, line 22 "loewr" should be --- lower --- and "separatin" should be --- separation ---.

In claim 1, column 5, line 34, "drawing" should be --- draining ---.

In claim 1, column 5, line 34 "heavy" should be --- heavier ---.

In claim 4, column 6, line 5 "heavy" should be --- heavier ---.

Signed and Sealed this

Seventh Day of April, 1992

Attest:

HARRY F. MANBECK, JR.

Attesting Officer     Commissioner of Patents and Trademarks